United States Patent
Stephan

(10) Patent No.: US 9,421,301 B2
(45) Date of Patent: Aug. 23, 2016

(54) PROCESS FOR PREPARING AN OSTEOINTEGRATIVE SURFACE ON A CERAMIC BODY

(75) Inventor: Marc Stephan, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 706 days.

(21) Appl. No.: 13/574,905

(22) PCT Filed: Feb. 10, 2011

(86) PCT No.: PCT/EP2011/000616
§ 371 (c)(1),
(2), (4) Date: Sep. 5, 2012

(87) PCT Pub. No.: WO2011/098269
PCT Pub. Date: Aug. 18, 2011

(65) Prior Publication Data
US 2012/0319316 A1    Dec. 20, 2012

(30) Foreign Application Priority Data
Feb. 12, 2010  (EP) .................................... 10001452

(51) Int. Cl.
*A61C 13/00*    (2006.01)
*A61L 27/10*    (2006.01)
(Continued)

(52) U.S. Cl.
CPC ............... *A61L 27/10* (2013.01); *A61C 8/0006* (2013.01); *A61C 8/0012* (2013.01); *A61L 27/32* (2013.01); *C04B 41/009* (2013.01); *C04B 41/5048* (2013.01); *C04B 41/87* (2013.01);
(Continued)

(58) Field of Classification Search
CPC    B29C 41/08; B29C 41/46; B29C 2043/3455; A61L 27/32; A61L 13/0003; A61L 13/0022; A61L 2007/004
USPC .......... 264/16, 17, 18, 19, 20; 427/2.26, 2.27, 427/2.29, 427
See application file for complete search history.

(56) References Cited

U.S. PATENT DOCUMENTS

| 5,456,723 A | 10/1995 | Steinemann |
| 5,934,287 A | 8/1999 | Hayashi et al. |

(Continued)

FOREIGN PATENT DOCUMENTS

| DE | 10 2006 062 712 A1 | 8/2007 |
| DE | 10 2007 057917 B3 | 5/2009 |

(Continued)

OTHER PUBLICATIONS

Li et al, Characterization of hydroxyapatite/nano-zirconia composite coatings deposited by high velocity oxy-fuel (HVOF) spray process, 2004, Surface and Coatings Technology, 182, pp. 227-236.*

(Continued)

*Primary Examiner* — Timothy Kennedy
(74) *Attorney, Agent, or Firm* — Oliff PLC

(57) ABSTRACT

Process for preparing an osteointegrative surface on a ceramic body by chemically modifying at least a part of the surface of the body. The process includes the subsequent steps of depositing a calcium phosphate mineral on the surface of a ceramic basic body by projecting agglomerates of particles comprising the calcium phosphate mineral towards the basic body, and heating the basic body with the calcium phosphate mineral deposited thereon.

18 Claims, 4 Drawing Sheets

(51) Int. Cl.

| | | |
|---|---|---|
| *A61C 8/02* | (2006.01) | |
| *A61C 8/00* | (2006.01) | |
| *A61L 27/32* | (2006.01) | |
| *C04B 41/87* | (2006.01) | |
| *C04B 41/00* | (2006.01) | |
| *C04B 41/50* | (2006.01) | |
| *C04B 111/00* | (2006.01) | |

(52) U.S. Cl.
CPC ......... *A61L 2400/18* (2013.01); *A61L 2430/12* (2013.01); *C04B 2111/00836* (2013.01)

(56) References Cited

U.S. PATENT DOCUMENTS

| | | |
|---|---|---|
| 6,102,703 A | 8/2000 | Day |
| 8,377,106 B2 | 2/2013 | Branemark et al. |
| 2004/0267376 A1 | 12/2004 | Suzuki et al. |
| 2005/0106534 A1 | 5/2005 | Gahlert |
| 2008/0213725 A1 | 9/2008 | Adilstam et al. |
| 2010/0081109 A1 | 4/2010 | Schlottig |

FOREIGN PATENT DOCUMENTS

| | | |
|---|---|---|
| EP | 0 388 576 A1 | 11/1989 |
| EP | 0 870 478 A1 | 4/1997 |
| EP | 0 864 332 A2 | 9/1998 |
| EP | 1 450 722 | 9/2004 |
| EP | 1 982 670 A1 | 4/2007 |
| EP | 2 002 799 A1 | 6/2007 |
| JP | H11-299879 | 11/1999 |
| JP | 2004-202126 | 7/2004 |
| JP | 2005-034630 | 2/2005 |
| JP | 2008-522714 | 7/2008 |
| WO | WO 8704110 A1 * | 7/1987 |
| WO | WO 03/045268 A1 | 6/2003 |
| WO | WO 2005/027771 A1 | 3/2005 |
| WO | WO 2005/115268 A1 | 12/2005 |
| WO | WO 2007/090529 A1 | 8/2007 |
| WO | WO 2008/077263 A2 | 7/2008 |

OTHER PUBLICATIONS

International Search Report and Written Opinion mailed Apr. 5, 2011 corresponding PCT/EP2011/000616.

Kim et al., Biomaterials 12 (2002), pp. 4113-4121 "Effect of $CaF_2$ on densification and properties of hydroxyapatite-zirconia composites for biomedical applications".

Adolfsson, et al., J. Am. Ceram. Soc., 83 [11] (2000), pp. 2798-2802, "Phase Analysis and Thermal Stability of Hot Isostatically Pressed Zirconia-Hydroxyapatite Composites".

Nayak et al., J. Mater Sci: Mater Med (2008), pp. 2437-2444, "Pressureless sintering of dense hydroxyapatite-zirconia composites".

Zhang et al., J. Am. Ceram. Soc., 89 [11] (2006), pp. 3348-3355, "Fabrication of Hydroxyapatite-Zirconia Composites for Orthopedic Applications".

* cited by examiner

US 9,421,301 B2

PROCESS FOR PREPARING AN OSTEOINTEGRATIVE SURFACE ON A CERAMIC BODY

FIELD OF THE INVENTION

The present invention relates to a process for preparing an osteointegrative surface on a ceramic body, as well as to said body. The invention further relates to the use of the body as an implant, in particular a dental implant.

BACKGROUND

Implants, such as dental implants, are well known in the art. They generally consist of a material, which is biocompatible and which additionally has a low elastic modulus and a high strength.

Apart from its biocompatibility and its mechanical properties, the osteointegrative properties of an implant are usually of major importance. The term osteointegration designates the direct structural and functional connection between living bone and the surface of the load-bearing implant. A good osteointegration means that the implant, after reaching a primary stability by screwing it into the bone, safely ossifies within a short healing time so that a permanent bond between implant and bone is obtained.

Dental implants which are currently in use are in general made of a metal, e.g. titanium, or a ceramic, e.g. a zirconia based ceramic, due to the biocompatibility and the favourable mechanical properties of these materials.

Alternatively to the materials mentioned above, it has further been suggested to use a material that closely resembles natural bone tissue, as an implant made of such a material would more fully integrate with existing bone tissue and enhance new bone growth around the implant. In this regard, the use of hydroxylapatite, which is very similar to the naturally occurring apatite, has been considered. Despite of the bioactive properties of implants formed from sintered hydroxylapatite, the mechanical properties of such implants have, however, turned out to be insufficient. For example, dental implants formed solely from hydroxylapatite are prone to crack and break after being implanted in a jaw bone.

Based on these observations, EP-A-0864332 suggests a method by which a coating of at least about 90% by weight of crystalline hydroxylapatite is applied on a metallic implant using plasma spraying.

Alternatively, U.S. Pat. No. 5,934,287 discloses a method by which particles formed of a material including hydroxylapatite are provided at a surface of a processed portion of a main body member formed of titanium or titanium alloy, such that each of said particles has a part embedded in said processed portion surface and a part protruding from said processed portion surface.

However, providing the surface of metallic implants with hydroxylapatite according to these methods has the disadvantage that the hydroxylapatite tends to be abraded when implanting the implant into the bone and subjecting it to physiological loading.

The development of the technology regarding osteointegrative properties of a metallic implant has thus gone off the coating of the surface with a bioactive material and has mainly focused on subtractive processes, as for example the one disclosed by EP-A-0388576.

Also with regard to the processing of the surface of a ceramic material, additive processes have been turned out to be problematic:

WO-A-2005/027771 relates to a process for preparing a dental installation in which a dispersion is applied on a substrate having a first porosity, said dispersion forming upon sintering a ceramic layer with a second porosity.

EP-A-0870478 relates to a dental retention element having a core of a high-strength material such as zirconia, said core being coated with a ceramic material which can be chemically and/or mechanically processed.

However, also the composite structures disclosed in WO-A-2005/027771 and EP-A-0870478 have the disadvantage that the ceramic coating is easily abraded.

A further alternative technique for providing a structure to the surface of a ceramic implant is described in DE-A-102006062712, which relates to a process in which the surface roughness is increased prior to the sintering by applying sharp-edged particles to the surface of the so-called green body and/or brown body. It is thereby preferred that the green body and/or the brown body is coated with a binder for fixation of the particles. According to another embodiment of the technique described in DE-A-102006062712, the particles are mixed with the binder and applied on the green body and/or the brown body.

DE-A-102006062712 thus teaches single particles to be applied on the surface of the implant body, which leads to protrusions in the shape of the particles. As mentioned above, it is according to DE-A-102006062712 essential that these particles are sharp-edged.

In order to prevent the implant to be damaged, DE-A-1020060621712 teaches that the particles are "trickled" on the green body and/or the brown body, respectively, without exerting pressure ("drucklos"). As illustratively shown in DE-A-1020060621712, a body with an interface between a basic body and the applied particles is thereby obtained.

The process according to DE-A-1020060621712 is however relatively complicated to perform. In particular with regard to the particles being trickled without exerting pressure, they tend to fall off the surface on which they are applied. Also, due to the fact that the trickled particles tend to accumulate in the valleys of the surface topography rather than on the peaks, a homogenous distribution of the particles is difficult to obtain.

Like for metallic implants, the development in providing an osteointegrative surface on a ceramic implant has thus gone off additive processes and has mainly focused on subtractive processes, as for example suggested by EP-B-1450722 and EP-A-1982670:

EP-B-1450722 relates to a dental implant made of zirconia ceramic which after abrasive blasting is subjected to a treatment using phosphoric acid, sulphuric acid, hydrochloric acid or mixtures thereof.

EP-A-1982670 relates to a process wherein a roughness is provided to the surface of the dental implant by sandblasting, milling and/or injection molding techniques prior to the etching of the implant with an etching solution comprising hydrofluoric acid.

SUMMARY OF THE INVENTION

Given the fact that subtractive techniques go along with a loss of material and might result in a negative impact on the mechanical stability of the implant, it would however be desirable to have an additive process which leads to an implant having an osteointegrative surface, said implant with said osteointegrative surface having at the same time a mechanical stability sufficient to withstand physiological loading.

The present invention relates to a process for preparing an osteointegrative surface of a ceramic body by chemically modifying at least a part of the surface of the body, said process comprising the subsequent steps of depositing a calcium phosphate mineral on the surface of a ceramic basic body by projecting agglomerates of particles comprising the calcium phosphate mineral towards the basic body and heating the basic body with the calcium phosphate mineral deposited thereon.

The present invention thus relates to an additive process.

By this process, a body can be obtained which has a surface region extending from the surface to a certain depth, said surface region comprising a calcium phosphate mineral. In this surface region, the density of the material gradually decreases in direction to the surface.

Specifically, the basic body with the calcium phosphate mineral deposited thereon is heated to a temperature at which the calcium phosphate mineral is integrated into the basic body.

More specifically, the basic body with the calcium phosphate mineral deposited thereon is heated to a temperature of at least 1100° C., preferably at least 1250° C., more preferably at least 1350° C., most preferably at about 1450° C.

It has been found that by heating to these temperatures, not only a calcium phosphate mineral is integrated into the basic body, but that calcium phosphate diffuses into the zirconia crystal lattice, which—depending on the degree of diffusion—leads to a stabilisation of the ceramic material of the body and ultimately to an improved ageing resistance. Also, the hydrophilicity of the body's surface is improved due to calcium being permeated into the zirconia crystal lattice.

As will be shown in detail below, the above temperatures are for example achieved during densely sintering the basic body in order to achieve maximum physical characteristics of the body. According to a further preferred embodiment, the temperature to which the basic body with the calcium phosphate mineral deposited thereon is heated is 1500° C. at most.

Due to the calcium phosphate mineral being integrated, there is after heating no calcium phosphate mineral coating in the narrower sense, and thus no interface between the calcium phosphate mineral and the basic body.

For the process of the present invention, any calcium phosphate mineral can be used. According to a preferred embodiment, the calcium phosphate mineral is selected from the group consisting of hydroxylapatite, fluorapatite, β (beta)-tricalcium phosphate and α (alpha)-tricalcium phosphate.

The surface obtained according to the process of the present invention has been found to be highly osteointegrative. Without wanting to be bound by the theory, this can on the one hand be explained by the fact that the calcium phosphate mineral used, and in particular tricalcium phosphate, such as α (alpha)- or β (beta)-TCP, hydroxylapatite or fluorapatite, is per se a bioactive material. On the other hand, a specific surface topography is formed due to the fact that agglomerates of particles are projected towards the surface of the ceramic basic body. Said surface topography includes cavities in the body's surface region and provides a specific roughness to the body. In addition to the composition of the surface comprising a bioactive material, said surface topography further contributes to the high osteointegrative properties of the body obtained.

Specifically, the agglomerates are projected towards the basic body by means of a carrier gas stream. This is in clear contrast to the trickling taught in DE-A-1020060621712.

More specifically, the agglomerates deform when impacting on the basic body such that the contact area between the agglomerates and the basic body is augmented during impacting.

The formation of the specific surface topography can thus be explained by the analogy of snowballs:

Given that the agglomerates according to the present invention generally deform like snowballs when impacting on the ceramic basic body, a good fixation of the deposited material is achieved due to the contact area between the agglomerate and the ceramic basic body being augmented during impacting. The deposited agglomerates roughly have the shape of elevations having a relatively large base area and tapering to a rounded apex.

In general, the agglomerates comprise a binder for binding the particles together. When using agglomerates comprising a binder, a particularly good fixation of the agglomerates on the surface of the basic body can be obtained. After deposition of the agglomerates, the binder can be removed during sintering, as will be described in detail below.

As explained above, the present invention allows the calcium phosphate mineral to be integrated into the basic body. There is thus no discrete interface on which separate particles are applied on, as is for example the case for an implant obtainable according to DE-A-102006062712. Thus, the problems of a coating that tends to fall off the interface can be circumvented by the present invention.

Using agglomerates of particles instead of discrete particles, the present invention also allows a homogenous surface roughness to be obtained in a very simple manner. As mentioned above, this is not the case for the method according to DE-A-102006062712. Applying the above mentioned snowball analogy, the trickling of separate particles taught by DE-A-102006062712 would correspond to the trickling of snowflakes which also tend to accumulate in the valleys of a topography rather than on the peaks and are thus not distributed homogenously.

The chemical modification according to the present invention can be carried out on the whole surface of the basic body or on parts thereof.

The present invention is particularly useful if the body is used as an implant, more particularly as a dental implant. If used as an implant, the process is preferably carried out such that the chemical modification is carried out at least on an area of the basic body designated to be embedded into a bone.

In contrast to implants made of titanium, which is dark and therefore mismatches with the color of natural teeth, the body of the present invention is based on a ceramic basic body and has thus the advantage that its color can be closely matched to the natural tooth color.

The basic body is preferably made of zirconia, alumina and/or a mixture of zirconia and alumina.

The ceramic material of the basic body is typically yttria- and/or ceria-stabilized. Other stabilizing agents, such as calcium, magnesium or scandium, are also thinkable.

Given the relatively demanding mechanical requirements for an implant, it is particularly preferred that the ceramic material of the ceramic basic body is yttria- and/or ceria stabilized zirconia due to the high strength that can be obtained by using said material.

According to a particularly preferred embodiment of the present invention, the agglomerates further comprise particles of a ceramic material, in particular of the ceramic material of the basic body. Thus, the deposited material is fully compatible with the material of the basic body. Alternatively, any other ceramic material which is compatible with the material of the basic body can be deposited.

In the preferred embodiment in which the agglomerates comprise a ceramic material apart from the calcium phosphate mineral, the volume ratio of the calcium phosphate mineral to the ceramic material preferably ranges from 1:100 to 60:100, more preferably from 10:100 to 40:100, most preferably from 20:100 to 30:100.

According to a preferred embodiment, the agglomerates have an average diameter ranging from 20 μm (micrometer) to 100 μm (micrometer), preferably from 40 μm (micrometer) to 70 μm (micrometer), leading to a surface having particularly high osteointegrative properties.

The grain size of the calcium phosphate mineral, and in particular of the hydroxylapatite, can be adjusted depending on the desired surface topography to be obtained. If the agglomerates further comprise particles of a ceramic material, the grain size of the calcium phosphate mineral is typically in the same range as the grain size of the ceramic particles.

The grain size of the ceramic particles is typically around 30 nm to 70 nm, for example about 360 Å (36 nm) when using zirconia powder of the grade TZ-3YSB-E (Tosoh Corporation).

Thus, the number of particles comprised by an agglomerate is in general in the range of several millions or billions.

The osteointegrative surface region formed according to the present invention and comprising a calcium phosphate mineral typically extends from the surface of the body to a depth of at most 500 μm (micrometer), preferably of at most 100 μm (micrometer), more preferably of at most 50 μm (micrometer). If the body of the present invention is a dental implant, the surface region extends from the surface to a depth ranging from 10 to 35 μm (micrometer).

Since according to the present invention agglomerates instead of single particles are projected towards the ceramic basic body, a sand-blasting apparatus can be used. The projection by a sand-blasting apparatus is particularly preferred, since it allows the parameters, such as the amount of material to be deposited, the blasting pressure, the blasting distance and the blasting duration, to be adapted to the respective needs. In particular, the parameters can be chosen in a manner such that the momentum of the agglomerates is high enough to ensure a good fixation of the agglomerates on the ceramic basic body's surface, but low enough to prevent damages on the surface.

The structure of the surface topography to be provided can in particular be controlled by adapting the blasting distance and thus the blasting cone.

If needed, the sand-blasting apparatus can further comprise means for cooling in order to prevent a melting of the organic fraction of the agglomerate at the blasting nozzle.

In general, the ceramic body is prepared by a sintering process. Respective sintering processes are known to the person skilled in the art and for example described in WO 2005/115268, the disclosure of which is incorporated herein by reference.

With regard to the sintering, the process of the present invention further comprises the subsequent steps of forming a green basic body comprising particles of a ceramic material and a binder, forming a brown basic body by removing the binder from the green basic body, and forming the ceramic body by sintering the brown basic body.

It is thereby particularly preferred that the agglomerates are deposited on the surface of the green basic body. This is due to the fact that the green basic body comprising the binder generally withstands the momentum of the agglomerates better than the brown basic body. Also, since according to this embodiment the basic body and the agglomerates deposited thereon are sintered in the same step, no cracks are formed which might arise due to the shrinkage of the material during sintering.

Preferably, the agglomerates are based on the ceramic material of which the green basic body is formed. To this ceramic material, the calcium phosphate mineral, in particular hydroxylapatite, is added.

Although hydroxylapatite is known to generally decompose to tricalcium phosphate when sintered in air at a temperature above 950° C., sintering processes have recently been developed in which the decomposition of hydroxylapatite is markedly suppressed or eliminated. In this regard, it is for example referred to Kim et al, Biomaterials 12 (2002), pp. 4113-4121, which teaches small amounts of $CaF_2$ (lower than 5 vol-%) to be added to zirconia-hydroxylapatite composites. A further technique for sintering zirconia-hydroxylapatite composites without any detectable decomposition of the hydroxylapatite is for example disclosed by Adolfsson, et al, J. Am. Ceram. Soc., 83 [11] (2000), pp. 2798-2802, using a closed system and thus reducing the fraction of vacancies formed when structural water is released. Further, Nayak et al, J Mater Sci: Mater Med (2008), pp. 2437-2444 aim to prepare a hydroxylapatite composite containing a uniform dispersion of $ZrO_2$ by a reverse strike precipitation route and to achieve a high sintered density of these composites with minimum decomposition of hydroxylapatite by pressure less sintering. In addition, Zhang et al, J. Am. Ceram. Soc., 89 [11] (2006), pp. 3348-3355 disclose a route to prepare zirconia-hydroxylapatite composites for orthopedic applications, starting from hydroxylapatite and zirconia powders dispersed in aqueous media with polyacrylic acid and glutamic acid as the dispersants and pressure less sintering of green samples formed therefrom. The disclosure of the articles by Kim et al, Adolfsson et al, Nayak et al and Zhang et al is herewith incorporated by reference.

As mentioned above, a body having particularly preferred mechanical properties is obtained when the ceramic basic body and/or the agglomerates comprise particles of yttria- and/or ceria stabilized zirconia. For example, an yttria-stabilized zirconia according to ISO 13356 is used. A specific example of a preferable yttria-stabilized zirconia is Tosoh zirconia powder of grade TZ-3YSB-E (Tosoh Corporation) comprising 4.95 to 5.35 wt-% $Y_2O_3$, 0.15 to 0.35 wt-% $Al_2O_3$, at most 0.02 wt-% $SiO_2$, at most 0.01 wt-% $Fe_2O_3$, at most 0.04 wt-% $Na_2O$ and comprising a binder in an amount corresponding to an Ig-loss of 2.7 to 3.9 wt-%, the percentages being based on the total weight of the zirconia powder.

According to a preferred embodiment, the process further comprises after sintering the brown basic body the step of thermal post-processing, in particular hot isostatic pressing (HIP), of the body.

In general, the hot isostatic pressing includes—after treatment of the ceramic body in an inert pressurizing gas—the treatment of the body in air.

According to a further aspect, the present invention relates to a body obtainable by the process described above. Said body comprises a surface region extending from the surface of the body to a certain depth. Said surface region comprises a calcium phosphate mineral, in particular hydroxylapatite. Preferably, the surface region comprising the calcium phosphate mineral is formed at least on an area of the basic body designated to be embedded into a bone.

In this regard, the body is preferably used as an implant, more preferably as a dental implant, as mentioned above.

A specific example of a process according to the present invention is given in the following:

EXAMPLES

Example 1

About 5 g of a zirconia powder of the grade TZ-3YSB-E (Tosoh Corporation) defined above, the crystallites having a grain size of about 360 Å has been pressed by a double-acting powder compressing tool (Fa. Paul-Otto Weber Maschinen- and Apparatebau GmbH; Model 20; size II, diameter 20 mm) using a press (Zwick Universalprüfmaschine) with a pressing force of about 110 MPa (about 34.5 kN). Thereby, green basic bodies having a density of about 2.8 g/cm$^3$ are obtained.

A granulate formed by agglomerates of particles comprising zirconia and hydroxylapatite was prepared in accordance with the method described by Zhang et al, Fabrication of Hydroxyapatite-Zirconia Composites for Orthopedic Applications, J. Am. Ceram. Soc., 89 [11] (2006), pp. 3348-3355.

The granulate was loaded into a sandblasting-apparatus (Renfert Basic Quattro) and the agglomerates were projected towards the green basic body for about 2 to 3 seconds under a blasting pressure of about 5.5 bar and at a blasting distance of about 14 cm.

The green bodies comprising the agglomerates applied thereon were then treated in a high-temperature kiln (Mihm-Vogt-Hochtemperaturofen HT) in accordance with the following program:
  a) heating at a heating rate of 1° C./min to 600° C. and maintaining the temperature at 600° C. for 2 hours to obtain a brown body;
  b) heating at a heating rate of 5° C./min to 1450° C. and maintaining the temperature at 1450° C. for 2 hours to obtain a fully sintered (white) body;
  c) cooling at a cooling rate of 10° C./min down to 1000° C. and then cooling naturally from 1000° C. to room temperature.

BRIEF DESCRIPTION OF THE FIGURES

The invention is further illustrated by way of the attached figures, of which.

DETAILED DESCRIPTION

Figure 1:
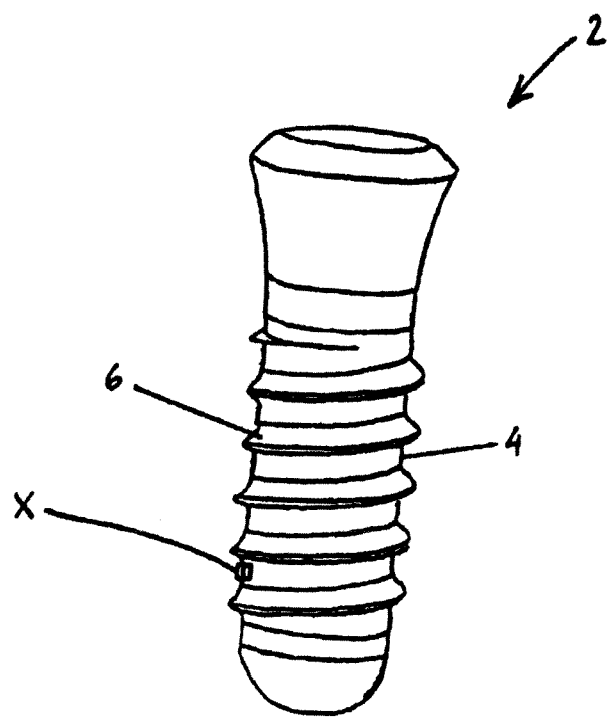
FIG. 1 is a perspective view of a body according to the present invention in the form of a dental implant.

As can be seen from FIG. 1, the dental implant 2 comprises a bone contact surface 4 intended to be embedded into the bone and comprising a threaded portion 6.

In order to allow for a good primary stability of the dental implant after implantation, at least the bone contact surface 4 is provided with a surface roughness according to the present invention.

Figure 2:
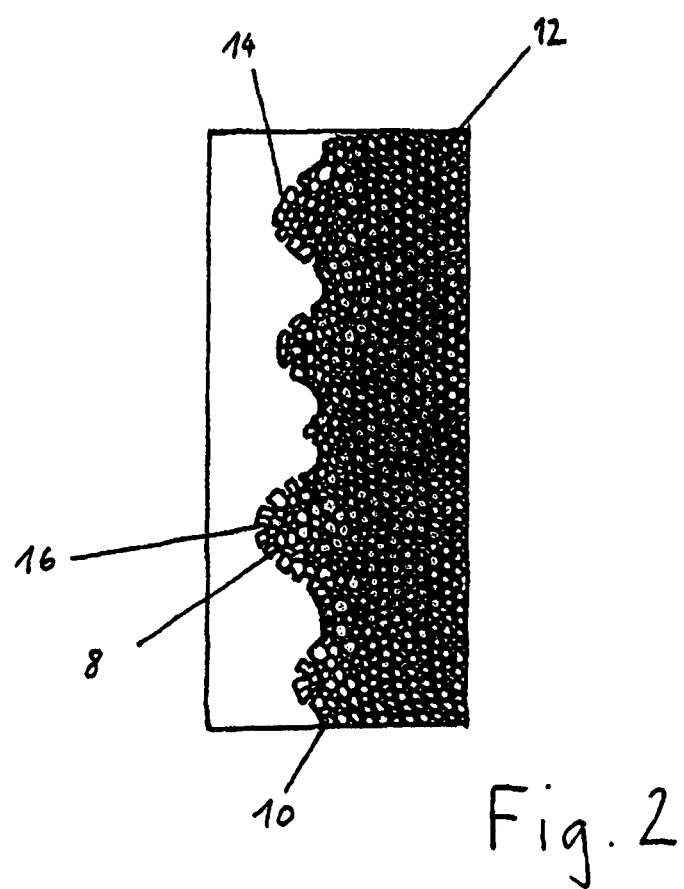
FIG. 2 shows schematically a cross-sectional view of sector X of FIG. 1.

As given in FIG. 2, the surface roughness is formed by agglomerates 8 of particles 10 comprising a calcium phosphate mineral, said agglomerates 8 being projected toward a basic body 12. When impacting on the basic body 12, the agglomerates 8 are deformed, thus resulting in a "macroroughness" which can be described by the above mentioned snowball-analogy. Due to the specific process of the present invention, there is no discrete interface between the basic body 12 and the particles 10 applied, but a density gradient that continuously decreases in direction to the surface 14. This continuous decrease of the density goes along with an increase of the porosity, leading to cavities 16 in the surface 14 forming a "microroughness".

Due to the chemical composition of the surface region formed and the specific surface topography obtained, the bone contacting surface 4 of the dental implant 2 is highly osteointegrative.

Figure 3:
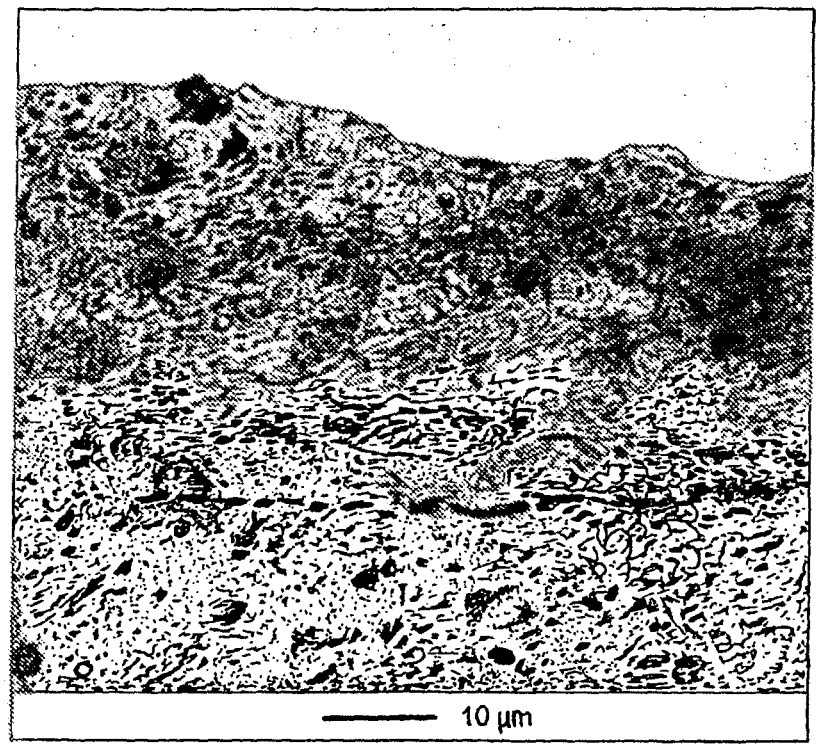
FIG. 3 is an SEM picture of the surface region of a body obtained according to the above example in cross-sectional view, the scaling given on the bottom of the picture corresponding to 10 μm (micrometer)

The effect that no discrete interface between the basic body and the particles applied is formed, can further be seen from the SEM picture according to FIG. 3. Also, the density gradient mentioned above, which continuously decreases in direction to the surface, can be seen from said SEM picture.

Figure 4:
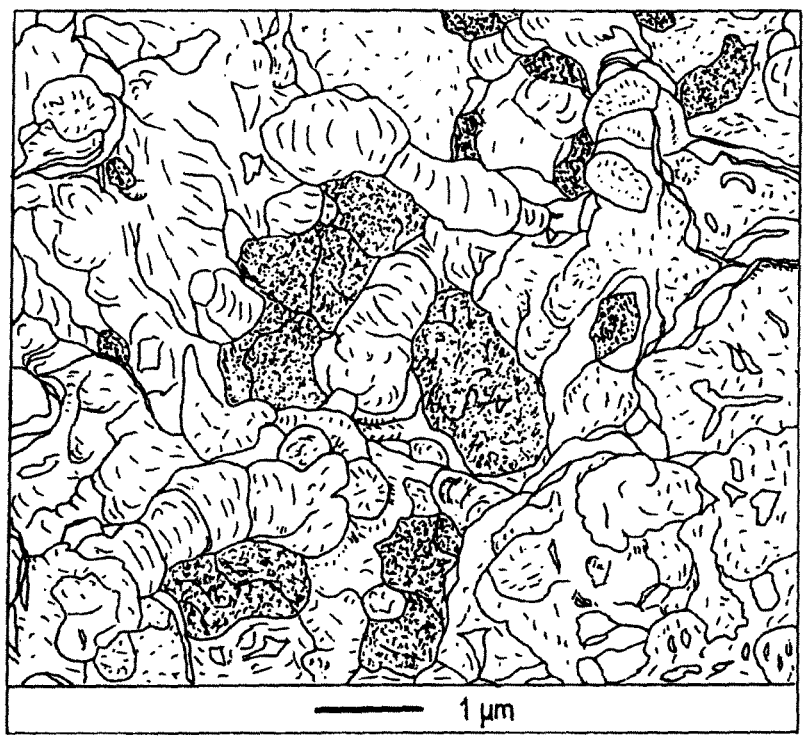
FIG. 4 is an SEM picture of a surface area of a body obtained according to the above example in top view, the scaling given on the bottom of the picture corresponding to 1 μm (micrometer).

The specific surface topography obtainable according to the present invention by projecting agglomerates of particles towards the surface of the basic body, is shown in the SEM picture according to FIG. 4. Said surface topography includes cavities in the body's surface region and has a surface roughness contributing to the osteointegrative properties of the body.

The invention claimed is:

1. A process for preparing an osteointegrative surface on a ceramic body by chemically modifying at least a part of the surface of the body, said process being an additive process and comprising:
   depositing a calcium phosphate mineral on the surface of a ceramic basic body by projecting agglomerates of particles comprising the calcium phosphate mineral towards the basic body, and
   heating the basic body with the calcium phosphate mineral deposited thereon;
   wherein a momentum of the agglomerates being projected towards the basic body is high enough to provide fixation of the agglomerates on the surface of the basic body and low enough to prevent damage to the surface of the basic body due to impact of the agglomerates with the basic body.

2. The process according to claim 1, wherein the basic body with the calcium phosphate mineral deposited thereon is heated to a temperature at which the calcium phosphate mineral is integrated into the basic body.

3. The process according to claim 1, wherein the basic body with the calcium phosphate mineral deposited thereon is heated to a temperature of at least 1100° C.

4. The process according to claim 1, wherein the calcium phosphate mineral is selected from the group consisting of hydroxylapatite, fluorapatite, β (beta)-tricalcium phosphate, and α (alpha)-tricalcium phosphate.

5. The process according to claim 1, wherein the agglomerates comprise a binder for binding the particles together.

6. The process according to claim 1, wherein the agglomerates are projected towards the basic body by means of a carrier gas stream.

7. The process according to claim 1, wherein the agglomerates deform upon impact with the basic body such that a contact area between the agglomerates and the basic body is augmented during impact.

8. The process according to claim 1, wherein the basic body is made of zirconia, alumina, and/or a mixture of zirconia and alumina.

9. The process according to claim 8, wherein the basic body is made of yttria- and/or ceria-stabilized zirconia.

10. The process according to claim 1, wherein the agglomerates further comprise the ceramic material of the basic body.

11. The process according to claim 1, wherein the agglomerates have an average diameter ranging from 20 μm to 100 μm.

12. The process according to claim 1, wherein the agglomerates are projected towards the basic body by a sand-blasting apparatus.

13. A process for preparing an osteointegrative surface on a ceramic body by chemically modifying at least a part of the surface of the body, the process being an additive process and comprising:
    forming a green basic body comprising particles of a ceramic material and a binder,
    depositing a calcium phosphate mineral on the surface of the green basic body by projecting agglomerates of particles comprising the calcium phosphate mineral towards the green basic body,
    forming a brown basic body by removing the binder from the green basic body with the calcium phosphate mineral deposited thereon, and
    forming the ceramic body by sintering the brown basic body;
    wherein a momentum of the agglomerates being projected towards the green basic body is high enough to provide fixation of the agglomerates on the surface of the green basic body and low enough to prevent damage to the surface of the green basic body due to impact of the agglomerates with the green basic body.

14. The process according to claim 13, further comprising thermal post-processing of the ceramic body after sintering the brown basic body.

15. The process according to claim 3, wherein the temperature is at least 1250° C.

16. The process according to claim 3, wherein the temperature is at least 1350° C.

17. The process according to claim 3, wherein the temperature is at least 1450° C.

18. The process according to claim 11, wherein the agglomerates have an average diameter ranging from 40 μm to 70 μm.

* * * * *